United States Patent [19]

Nelson et al.

[11] Patent Number: 4,623,500
[45] Date of Patent: Nov. 18, 1986

[54] METHOD OF MOUNTING A PLURALITY OF COUPONS IN MOLDED MATERIAL AND POLISHING SURFACES THEREOF FOR CROSS-SECTIONAL ANALYSIS OF PRINTED CIRCUIT BOARDS

[75] Inventors: James A. Nelson, Mundelein; Robert E. Zimmer, Niles, both of Ill.

[73] Assignee: Buehler Ltd., Lake Bluff, Ill.

[21] Appl. No.: 724,754

[22] Filed: Apr. 18, 1985

Related U.S. Application Data

[62] Division of Ser. No. 618,476, Jun. 8, 1984, Pat. No. 4,534,536.

[51] Int. Cl.⁴ ..................... B29C 39/10; B29C 37/02
[52] U.S. Cl. .................................. 264/162; 264/263; 264/271.1; 264/272.17; 356/244
[58] Field of Search ..................... 264/263, 271.1, 162, 264/272.17; 356/244

[56]    References Cited
U.S. PATENT DOCUMENTS 2,378,252   6/1945   Staehle et al. .................. 264/273 X Primary Examiner—Philip Anderson
Attorney, Agent, or Firm—Charles F. Pigott, Jr.

[57]    ABSTRACT

Method and apparatus for high volume preparation of cross-sectional specimens of printed circuit boards for microscopic examination, including a method and apparatus for precision mounting of a large number of such cross sections in a single molding sequence for simultaneous polishing of such cross sections in a single polishing operation.

4 Claims, 14 Drawing Figures

METHOD OF MOUNTING A PLURALITY OF COUPONS IN MOLDED MATERIAL AND POLISHING SURFACES THEREOF FOR CROSS-SECTIONAL ANALYSIS OF PRINTED CIRCUIT BOARDS

This is a division of application Ser. No. 618,476, filed June 8, 1984 and now U.S. Pat. No. 4,534,536.

BRIEF SUMMARY OF THE INVENTION

Microscopic examination of polished cross sections provides the most comprehensive means of monitoring printed circuit board production. By means of microscopic examination of selected cross sections, it is possible to determine printed circuit board quality at various critical stages of production. By thus detecting problems in the earlier stages of processing, excessive added costs due to defective material can be avoided, and higher yields can be obtained.

The need for high volume analysis of printed circuit boards is the result of an ever increasing demand for thorough quality control in high production shops. One reason relates to certain military specifications which set forth strict requirements for testing of printed circuit boards, one requirement being that one coupon or cross section containing a minimum of three plated-through holes must be made from each plated panel.

In the past it has been common to use manual preparation techniques to prepare polished cross sections of printed circuit boards for microscopic examination. Such manual techniques include a manual polishing operation where a single cross section is manually held against a rotating abrasive platen to polish such a cross section one at a time. Increased demand for polished microsections requires that high volume techniques be used, whereby many such cross sections may be polished simultaneously in a single series of polishing operations. However, the requirement for such mass polishing of many cross sections in a single polishing operation is challenging due to the requirement for extreme precision in such polishing.

One important requirement in such sample preparation is that the final plane of polish must be through the centerline axis of all test holes. In other words, each coupon or cross section comprises a section which is stamped or otherwise removed from a plated printed circuit board panel, and such specimen section includes one cross-sectional edge which must be polished for microscopic examination. In accordance with certain military specifications referred to above, the polished cross-sectional edge of such specimen coupon which will be subjected to microscopic examination must contain a minimum of three plated-through holes.

After the polishing of the cross-sectional edge, it is required that the final polished surface define a plane which passes through the centerline or is close to the centerline of all three plated-through holes. Moreover, where fifty or more specimen coupons are polished simultaneously in a single high volume polishing operation, it is important that the final polished cross-sectional surface on each one of those coupons be close to the centerline axis of each of the holes in that specimen coupon.

Accordingly, there are special problems in meeting the foregoing accuracy requirements while at the same time effecting high volume production of polished cross sections. Thus, if the polished surface on a given coupon specimen is not at the centerline axis of each of the through holes in the coupon, the observed layer may be distorted and a measuring or interpretation error may result during microscopic examination.

It is therefore an object of our invention to develop a method and apparatus for providing a high volume of acceptably polished cross sections of printed circuit boards where the polished cross-sectional surfaces are close to the centerline axis of a plurality of through holes in each coupon specimen.

It is another object of our invention to provide a method and apparatus for producing such cross sections using a minimum number of preparation steps consistent with good metallographic sample preparation practice.

A further object is to provide a method and apparatus for producing such cross sections by a method which achieves good results even when operated by relatively unskilled persons.

The foregoing and other objects and advantages of the invention will be apparent from the following description of a preferred embodiment, taken in conjunction with the accompanying drawings.

Now, in order to acquaint those skilled in the art with the manner of making and using our invention, we shall describe, in conjunction with the accompanying drawings, a preferred embodiment of the invention.

DETAILED DESCRIPTION OF THE INVENTION

Figure 1:
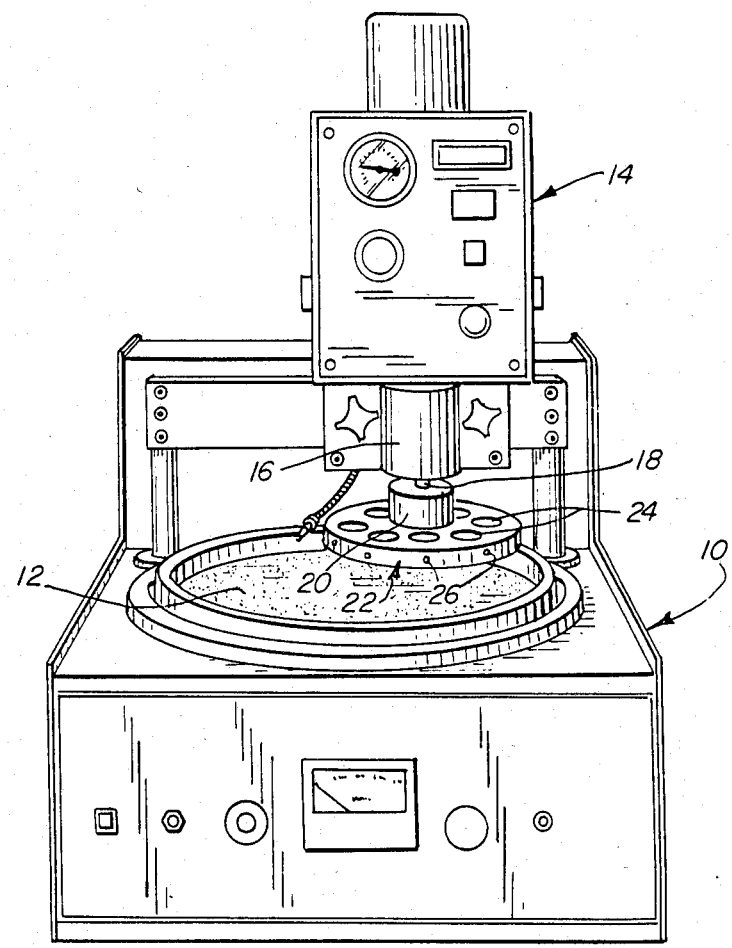
FIG. 1 is a perspective view of a high performance polishing machine which may be used in conjunction with the present invention to polish a large number of specimen coupons in a single polishing operation.

FIG. 1 shows a known form of polishing machine of a type suitable for use with the present invention and comprising a main housing 10 on which a rotatable platen 12 is mounted, and an upper housing 14 from which an air cylinder 16 depends. A drive shaft 18 projects from the bottom of air cylinder 16, the shaft 18 being rotated by an electric motor (not shown) and being movable vertically by the air cylinder 16. A chuck 20 has a sample holder 22 fixed thereto, and the chuck is removably attached to the drive shaft 18. The sample holder 22 includes a plurality of holes 24 arranged in a circle, and each hole is suitable for holding a mounted specimen to be polished.

Each specimen to be polished is normally mounted in a plastic mount to facilitate handling, such mounting being effected so the specimen surface to be polished is approximately flush with one surface of the plastic mount. The plastic mount is held in a selected opening 24, such as by adjustable screw means 26, and the mount is oriented in the sample holder 22 so the specimen surface to be polished projects beneath the bottom surface of the specimen holder a predetermined amount so the specimen surface may be held against the platen 12 on which abrasive material is applied.

In the foregoing manner, a plurality of mounted specimens may be fixtured in respective openings 24 in the sample holder 22, the chuck 20 secured to the sample holder, the chuck with attached sample holder secured to drive shaft 18, the platen 12 with an abrasive paper disc mounted threeon rotated at a selected speed, the sample holder 22 rotated in a selected direction at a desired speed, and the pressure cylinder 16 actuated to move the sample holder 22 downwardly to force the specimens to be polished against the rotating abrasive platen 12 at a desired pressure, thereby causing the coupon specimens to be polished. Since the sample holder 22 includes several openings 24 for fixturing mounted specimens, a large number of specimens may be polished during a single operation.

The present invention relates to a method and apparatus which permits high volume polishing of a plurality of printed circuit board cross sections using polishing apparatus of the type described above. Such apparatus includes means for mounting sections taken from printed circuit board panels, referred to as coupons, and mounting the coupons in plastic mounts which facilitate subsequent handling and polishing. In accordance with known procedures, we prefer to mount a plurality of coupons in an assembly by pinning them together, and thereafter the pinned coupon assembly is cast in a plastic mount using apparatus constructed in accordance with the present invention.

Figure 2:
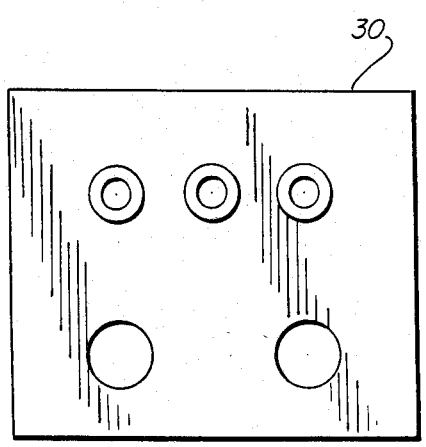
FIG. 2 is a plan view showing a specimen coupon which has been punched or sheared from a plated printed circuit board panel.
Figure 3:
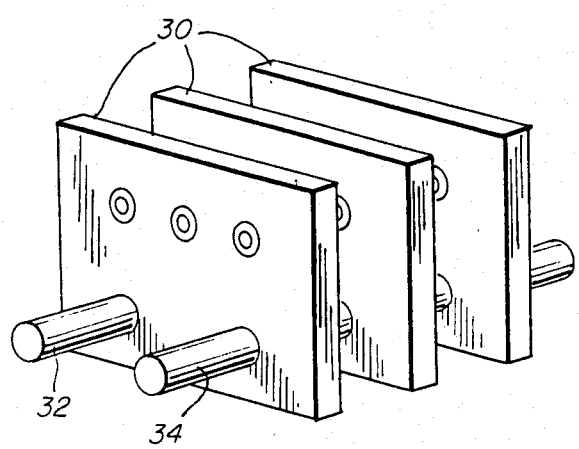
FIG. 3 is a perspective view showing a plurality of coupons mounted on a pair of index pins to form a coupon assembly which will be cast in a resin mount to permit simultaneous polishing of a cross-sectional surface on each of the plurality of coupons.

FIG. 3 shows a plurality of coupons 30 which are pinned together by a pair of index pins 32 and 34. Each coupon 30 comprises a small portion from a plated printed circuit board panel for testing purposes. The coupons are taken from a standard I.P.C. test pattern, and they are removed from a printed circuit board panel by a shearing or punching operation. The preferred shape of the coupon as shown in FIG. 2 may ultimately be set by standard specifications, the coupons shown herein being generally rectangular in shape and, as indicated above, including at least three plated-through holes at the cross-section or edge portion to be polished and inspected.

We consider the foregoing pin reference method as the most reliable for assembling a plurality of coupons in a predetermined relationship so that they may be cast in a common mount for polishing a given cross section on each in a common polishing operation. Such a pin reference technique permits establishment of a precise datum point relative to a required cross-sectional plane to be polished and examined, namely, a plane which passes through the centerline axis of at least three test holes in each coupon.

In order to produce a pinned coupon assembly as shown in FIG. 3, it is necessary to drill a pair of holes in each coupon, which holes must be of a specific size and location, as is known in the art, to accept pins which are dimensionally stable. In accordance with the present invention, the index pins 32 and 34 are disposable precision pins so it is not necessary to remove the pins for re-use afer the pinned assembly has been cast in a block of mounting resin.

Such use of disposable pins permits filling a mold with resin material so it encompasses the index pins, as contrasted with the usual procedure where the pins are positioned at a location above the level to which resin material is poured in the mold. It is preferred to utilize a fixture to facilitate insertion of the pins through the coupons, and it is desirable to space the coupons 30 on the index pins 32 and 34 to provide space between each coupon sufficient to allow the flow of resin material into the holes during the molding operation.

Figure 6:
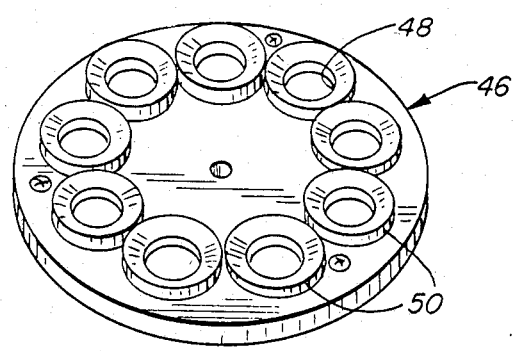
FIG. 6 is a perspective view of a mold top member having a plurality of holes arranged in a circle to correspond with the similar holes in the mold base and the sample holder, there being an individual pouring lip removably mounted in each of the holes to facilitate the pouring of molding material.
Figure 5:
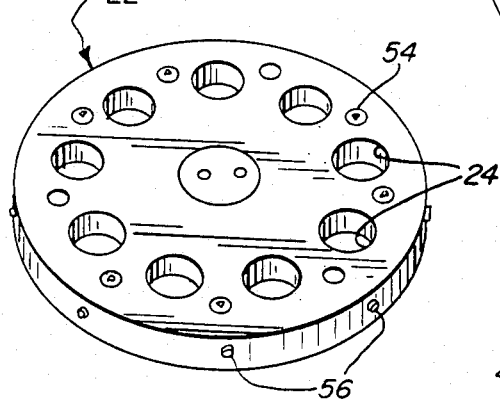
FIG. 5 is a perspective view of a sample holder comprising a metal plate with a plurality of holes arranged in a circle for containing respective pinned assemblies of coupons of the type shown in FIG. 3.
Figure 4:
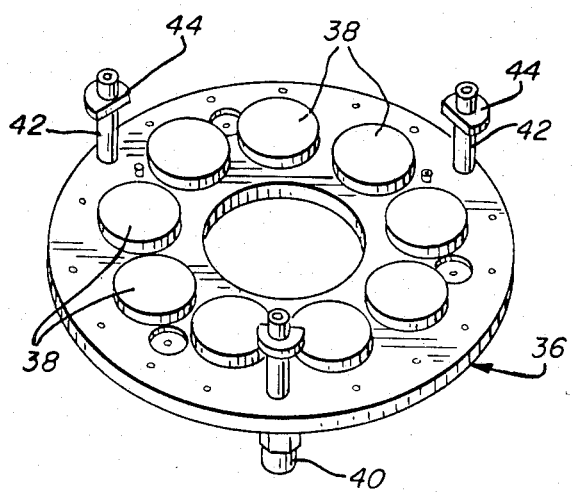
FIG. 4 is a perspective view of a metal mold base having a plurality of holes formed therein and arranged in a circle, and an individual rubber mold base member removably mounted in each of the holes.

Reference is now made to FIGS. 4-6 which illustrate the three principal components of a mold assembly. FIG. 4 shows a mold base comprising a disc-shaped metal base member 36 having a plurality of holes arranged in a circle, each such hole having an individual silicone rubber mold base 38 removably mounted therein. The base plate 36 is provided with three spaced feet 40 so the plate may be supported on the feet and spaced somewhat above a countertop or other supporting surface. Located above each of the feet 40 is an upwardly projecting threaded shaft 42 on which clamp washer 44 or the like is mounted for a purpose to be described hereinafter.

FIG. 5 shows the sample holder 22 having the plurality of holes 24 each of which defines a portion of a mold compartment in which one of the pinned coupon assemblies of FIG. 3 is positioned for purposes of a molding operation. In the assembly of the mold components, the sample holder 22 is positioned on top of the mold baseplate 36. The outer diameter of the sample holder 22 is less than the diameter of the circle defined by the threaded shafts 42 which project up from the baseplate 36, so holder 22 may be placed on top of baseplate 36 within three posts 42.

Reference is now made to FIG. 6 which shows a mold top plate 46 having a plurality of holes 48 arranged in a circle and corresponding to the number and location of the holes 24 in the sample holder 22 and the holes in the baseplate 36. The mold top plate 46 is made of metal and has an outer diameter approximately equal to the diameter of the sample holder 22, although like the baseplate 36 is may be thinner than the sample holder 22. Each of the holes 48 has an individual silicone rubber pouring lip 50 removably mounted therein to define an entrance to the corresponding mold chamber. When the mold components are assembled, the top plate 46 is mounted directly on top of the sample holder 22, as will be described more fully hereinafter.

In order to carry out a molding operation, sample holder 22 is mounted on top of the mold baseplate 36 with the openings 24 in sample holder aligned with the individual rubber mold bases 38 mounted in the plate 36. Thus, each opening 24 forms a molding chamber, and each rubber base member 38, which has a generally flat top surface, forms a base for a molding chamber.

Figure 7:
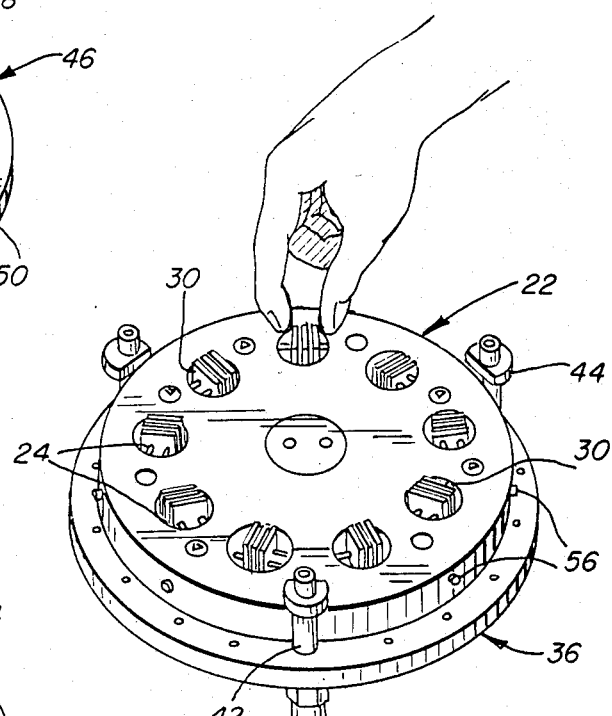
FIG. 7 is a perspective view showing the sample holder of FIG. 5 mounted on top of the mold base of FIG. 4, and showing an operator placing pinned coupon assemblies of the type shown in FIG. 3 into respective openings in the sample holder preparatory to a molding operation.

As shown in FIG. 7, after holder 22 is positioned on top of baseplate 36, one of the pinned coupon assemblies is positioned in each of the mold chambers 24 in a manner so the cross-sectional coupon surfaces to be polished are facing upwardly. It will further be seen from FIG. 7 that such coupon surfaces project above the planar top surface of the sample holder 22, which is essential for the subsequent polishing operation. In the embodiment shown, the sample holder 22 has nine cavities 24, and thus nine pinned coupon assemblies are mounted in the sample holder for each molding operation.

Figure 8:
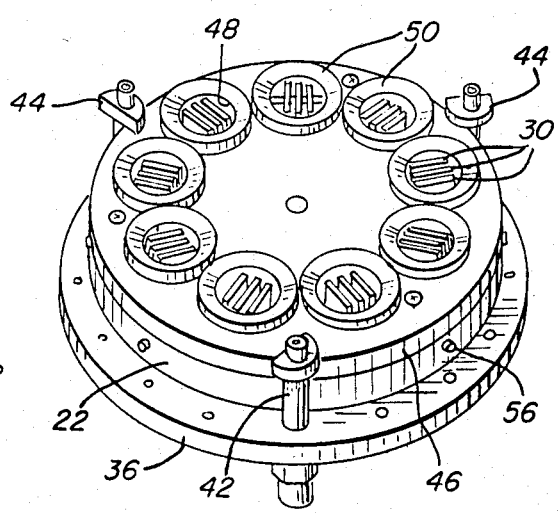
FIG. 8 is a perspective view showing the mold top member of FIG. 6 mounted on the top of the assembly of FIG. 7 to provide a complete mold assembly.

The next step in the assembly of the mold is shown in FIG. 8 where the mold top place 46 is placed on top of the sample holder 22 with the top plate openings 48 in alignment with the holes or cavities 24 in the sample holder. It will thus be seen that the rubber pouring lips 50 form entrance portions to each of the mold cavities. Moreover the pouring lips 50 are high enough to permit the resin molding material to substantially cover the various pinned coupons 30, it being preferred that the top of the resin level be approximately flush with the cross-sectional surfaces to be polished. As also shown by FIG. 8, the clamp washers 44 are adjusted on the threaded rods 42 to secure mold top plate 46 in position and thereby hold the mold components in a stacked assembly.

Once the mold assembly is secured as shown in FIG. 8, cast mounting resin is poured into each of the mold cavities. In accordance with the present invention it is preferred that the resin material be poured to a level approximately flush with the coupon cross-sectional surfaces to be polished. The foregoing procedure will provide optimum support for the mounted coupons during subsequent grinding and polishing, although normally it is permissible if the coupon surfaces to be polished project a limited extent from the plastic mount.

Figure 9:
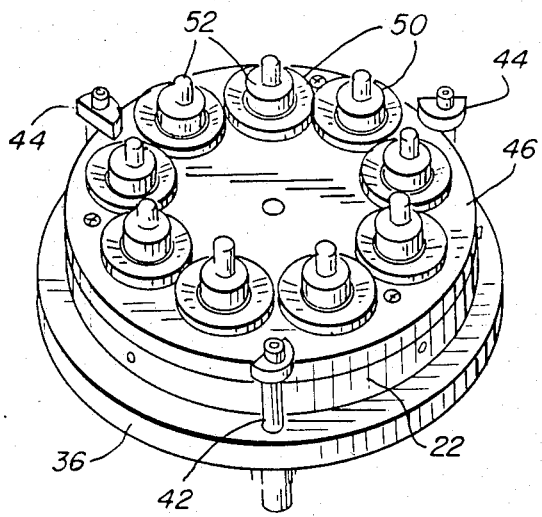
FIG. 9 is a perspective view of the mold assembly of FIG. 8 showing weights which may be placed on the top of each of the pinned coupon assemblies after mounting resin has been poured into each of the mold openings.

A suitable resin is Sampl-Kwick acrylic resin sold by Buehler Ltd. of Lake Bluff, Ill., which resin cures in 5 to 7 minutes and is well known in the industry. FIG. 9 shows an optional feature comprising the placing of a weight 52 on top of each of the pinned coupon assemblies during the curing of the resin mounting material.

It is important to understand that in accordance with the present invention the pinned coupon assemblies are cast in resin mounting material directly in the sample holder 22 as contrasted with mounting them by means of a separate molding operation and then positioning the plastic mounts in the sample holder 22 for a subsequent polishing operation. Thus, by casting the pinned coupon assemblies directly in their plastic mounts while they are in the sample holder 22, great accuracy may be acheived with respect to the positioning of the pinned coupons relative to one another in the common sample holder 22, and the step of removing the mounted pinned assemblies from a mounting device and then positioning the mounted devices in the sample holder is entirely eliminated. Moreover, by using disposable pins 32 and 34, the time-consuming step of removing such pins after a molding operation is also eliminated.

Figure 10:
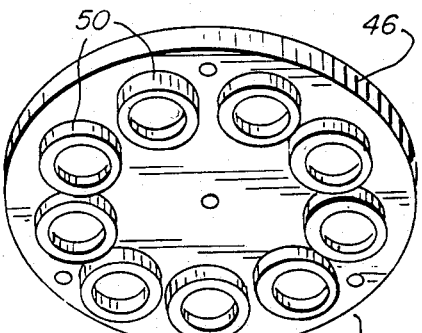
FIG. 10 is a view of the mold assembly after a molding operation when the mold top member has been removed.
Figure 11:
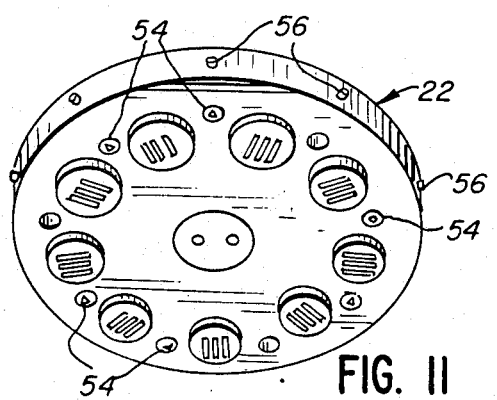
FIG. 11 is a perspective view of the bottom of the sample holder after a molding operation showing each of nine pinned coupon assemblies cast in individual cylindrical molds of transparent resin material to facilitate subsequent handling of the coupon assemblies.
Figure 11:
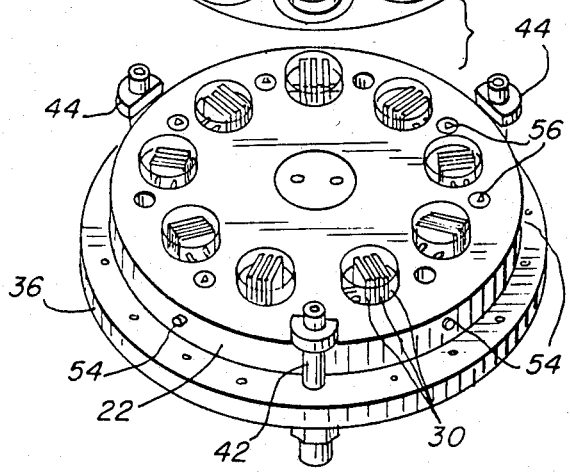

After the resin mounting material has cured, top plate 46 is removed as shown in FIG. 10, after which the sample holder 22 is removed, there being a cylindrical plastic mount located within each of the nine holes in the sample holder, and each mount encapsulating a pinned coupon assembly as shown in FIG. 11 in a manner such that the cross-sectional surfaces of the coupons to be polished and examined are approximately flush with the surface of the mount, or they project therefrom only a limited amount. FIG. 11 shows that the plastic mount surfaces project beyond the bottom surface of the sample holder 22, and as previously explained, the same is true of the cross-sectional coupon surfaces to be polished.

The sample holder 22 includes a plurality of diamond stops 54 which project beyond the bottom surface of the sample holder as shown in Fig. 11 by a predetermined amount which is set by adjustment members 56. The diamond stops 54 control the amount of material which is removed from the cross-sectional surfaces of the encapsulated coupons 30 during the subsequent polishing operation. The sample holder 22 into which the coupons 30 are cast is a precision tool which maintains the important dimensional relationships that are previously established between the index pins 32 and 34 and the test holes through the coupons 30. The diamond stops 54 are essential to establish the exact plane of polish, and such stops are pre-set by using a screwdriver or the like to adjust the screw members 56. A two-sided gauge plate is used during the setting of the diamond stops, one side being used to set the stops for a coarser grinding operation, and the second side being used to set the stops for a finer grinding step.

The next step is to attach the chuck 20 to the sample holder 22 and mount the chuck and attached sample holder on a polishing machine as described previously in conjunction with FIG. 1. For purposes of a polishing operation, the platen 12 has an abrasive paper disc mounted on its surface, either by mechanical means or by using pressure sensitive adhesive backed abrasive paper. A polishing machine which is well suited for use with the instant invention is sold by Buehler Ltd. of Lake Bluff, Ill., and is known as the Ecomet IV/Euromet I sample preparation machine.

Because the cylinder 16 of such a machine is air activated and well controlled, it is possible to apply a uniform, predetermined, and repetitive pressure when the mounted samples or coupons are pressed down against the abrasive platen 12 during a polishing operation. In accordance with the preferred embodiment described herein, the coupons 30 are substantially covered by the resin mounting material thereby supporting the coupons under load.

In accordance with a preferred grinding and polishing sequence, the diamond stops 54 are set to a coarse position, and grinding is carried on for aproximately 2 minutes until the stops touch on 120 grit silicon carbide abrasive paper applied to the platen 12. The sample holder 22 is then rinsed, and the stops 54 are reset to a fine setting, after which grinding is carried on for about 30 seconds until the stops touch on 600 grit silicon carbide paper. The stops 54 are then reset to be even with the face of the sample holder 22, and the holder is then cleaned in an ultrasonic clear cleaner for a maximum of 20 to 30 seconds.

Figure 12:
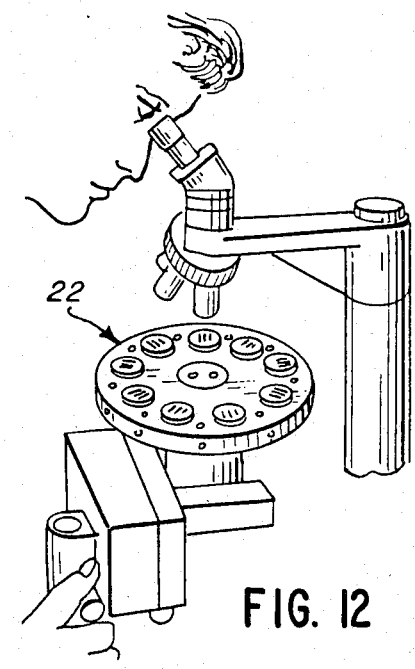
FIG. 12 is a perspective view showing an operator conducting a preliminary examination of the mounted coupon assemblies prior to removing coupon assemblies from the sample holders.

Thereafter, a polishing operation may be carried out using a napless polishing cloth such as sold by Buehler Ltd. under the name Texmet, which cloth is charged with 3 micron diamond paste and extender, the polishing operation being carried on for approximately 30 to 40 seconds. After another ultrasonic cleaning of the sample holder for 20 to 30 seconds, final polishing may be carried out using a napped polishing cloth such as sold by Buehler Ltd. under the name Microcloth, which cloth is charged with 0.05 micron alumina. For special quality, one may add a colloidal silica solution such as sold by Buehler Ltd. under the name Mastermet. The sample holder 22 with the mounted specimens therein is then rinsed, dried, and finally inspected under a microscope as shown in FIG. 12.

Figure 13:
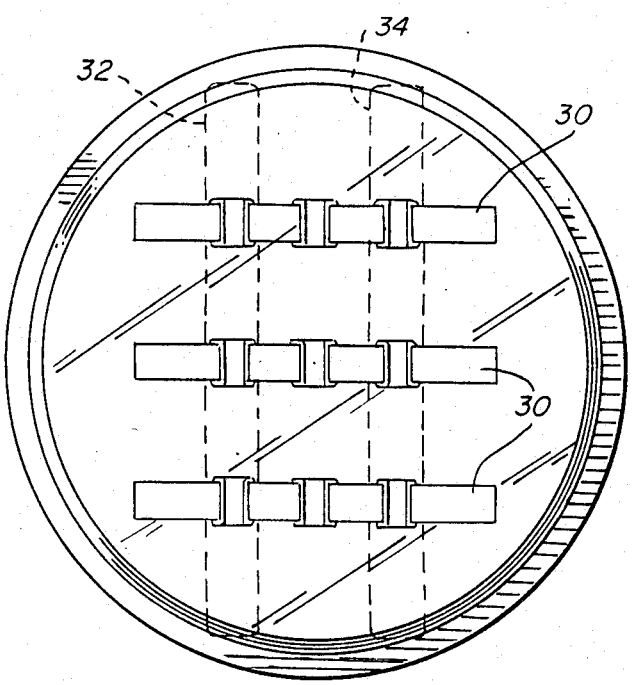
FIG. 13 is an enlarged top plan view of one of the mounted coupon assemblies after removal from a sample holder.
Figure 14:
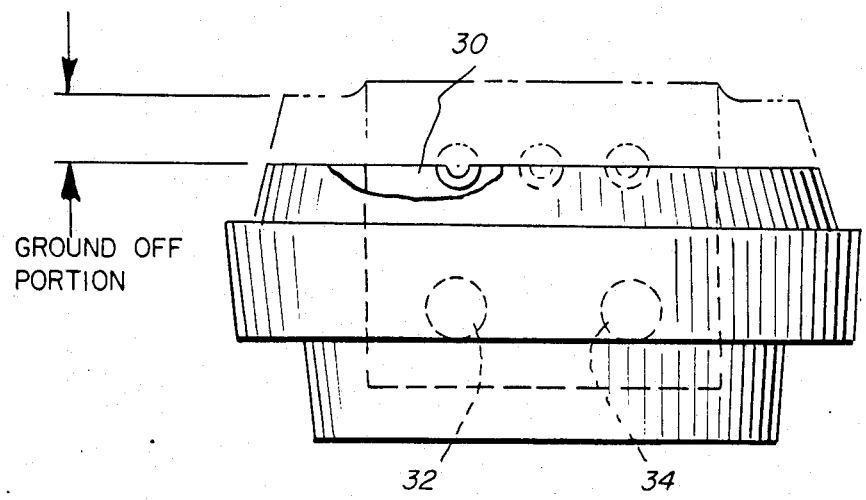
FIG. 14 is an enlarged elevational view of the mounted coupon assemblies shown in FIG. 13, the portion to be removed during a polishing operation being shown in dotted lines.

It is preferable to conduct a cursory examination of the polished cross-sectional surfaces of the coupons 30 before removing the mounted coupons from the sample holder 22, in the event some further polishing of the cross-sectional surfaces is indicated. If such an inspection indicates acceptable polishing results, the individual mounted samples may then be removed from the sample holder 22 using a simple knock-out procedure. For example, a punch member which slides in a guide may be positioned on top of the sample holder for punching and loosening the individual plastic mounts so they may be manually removed for purposes of subsequent microscopic inspection of the polished cross sections. FIG. 13 shows a top plan view of a mounted coupon assembly after a polishing operation, and the disposable pins 32 and 34 are shown in dotted lines. FIG. 14 is an elevational view of the mounted coupon assembly after a polishing operation and it can be seen from the drawing that the polished cross-sectional surface is approximately through the axis of the three plated-through holes which comprise the test holes to be inspected. The portion ground off during the polishing operation is shown in dotted lines.

Uses of the method and apparatus of the present invention achieves acceptably polished cross sections at a high volume rate where the polished cross-sectional surface of each of the many coupons is at or within plus or minus 0.005 inch of the centerline axis of a minimum of three through holes in each coupon. The foregoing applies where each mount contains a pinned assembly of 3 to 6 coupons, and where the sample holder 22 mounts from 8 to 15 mounted pinned coupon assemblies for simultaneous polishing in a single polishing operation.

What is claimed is:

1. A method of mounting a plurality of coupons taken from printed circuit board panels for purposes of polishing such coupons, said method comprising, in combination, pinning a plurality of coupons together in spaced relation using a pair of disposable pins which extend through each coupon on the side opposite the cross-sectional surface to be polished so as to form a pinned coupon assembly, placing said pinned assembly in a mold with the cross-sectional surfaces to be polished facing upwardly, and adding molding material to the mold to produce a pinned assembly mounted in a plastic mount.

2. A method as defined in claim 1 where the molding material is added to the mold substantially to the level of the cross-sectional surfaces to be polished.

3. A method as defined in claim 1 where a plurality of pinned assemblies are placed in respective openings in a sample holder, molding material is added in said openings to cast each pinned assembly in a plastic mount directly in said sample holder, and said sample holder is inverted and attached to a polishing machine for simultaneous polishing of said cross-sectional surfaces.

4. A method as defined in claim 3 where said sample holder includes at least three adjustable projecting stop members, and said stop members are adjusted to control the amount of material removed from said cross-sectional surfaces during the polishing thereof.

* * * * *